United States Patent [19]

Breuker

[11] 4,421,849

[45] Dec. 20, 1983

[54] METHOD FOR BIOLOGICAL SCREENING

[76] Inventor: Eberhard Breuker, Rektenstrasse 10, Detmold, Fed. Rep. of Germany, D-4930

[21] Appl. No.: 385,116

[22] Filed: Jun. 4, 1982

Related U.S. Application Data

[63] Continuation-in-part of Ser. No. 176,006, Aug. 7, 1980, abandoned.

[30] Foreign Application Priority Data

Aug. 11, 1979 [DE] Fed. Rep. of Germany ....... 2932694

[51] Int. Cl.³ .............................................. C12Q 1/18
[52] U.S. Cl. ......................................... 435/32; 435/29; 435/33; 435/287; 435/297; 435/298; 435/301; 435/803
[58] Field of Search ................... 435/32, 33, 287, 301, 435/297, 298, 29, 803

[56] References Cited

U.S. PATENT DOCUMENTS

| 2,761,813 | 9/1956 | Goetz ..................................... 435/33 |
| 2,992,974 | 7/1961 | Belcove ................................ 435/299 |
| 3,205,151 | 9/1965 | Landau ................................. 435/33 |
| 3,509,026 | 4/1970 | Sanders ................................ 435/33 |
| 3,585,112 | 6/1971 | Ernst .................................... 435/299 |
| 3,741,877 | 6/1973 | Shaufus ............................... 435/299 |
| 3,808,103 | 4/1974 | Buissiere ............................. 435/301 |
| 3,814,670 | 6/1974 | Freake ................................. 435/301 |
| 3,843,456 | 10/1974 | Haden ................................. 435/299 |
| 3,929,583 | 12/1975 | Sharpe ................................. 435/301 |
| 4,129,483 | 12/1978 | Bocher ................................ 435/301 |

Primary Examiner—Ernest G. Therkorn
Attorney, Agent, or Firm—Dennis P. Clarke

[57] ABSTRACT

Disclosed is a method of screening or identifying a microorganism by providing two microorganism nutrient medium layers in communication with and separated by a sterilizable membrane filter, implanting at least one of the layers with a microorganism, and allowing an effective substance to permeate through the filter to enable microorganism identification.

8 Claims, 1 Drawing Figure

METHOD FOR BIOLOGICAL SCREENING

RELATED U.S. APPLICATION DATA

This application is a continuation-in-part application of application Ser. No. 176,006, filed Aug. 7, 1980, now abandoned.

BACKGROUND OF THE INVENTION

In microbiological screening, reliance is often placed upon the fact that numerous organisms produce certain effective substances such as antibiotics, amino acids, enzymes, vitamins, toxins, etc., which react in a known manner with test microorganisms thereby identifying in a positive manner the microorganism producing the effective substance. For example, a test microorganism known to react in an identifiable manner with an antibiotic produced by a microorganism is contacted with the effective substance produced by the microorganism and the presence or absence of the identifiable reaction is detected thus identifying the microorganism.

Various apparatuses and methods have been suggested in the past for accomplishing such screening procedures. One approach involves the coating of a plate with the microorganisms suspected of producing the effective substance in the form of a colony and overcoating the unknown colony with a second layer of culture medium containing the test microorganism. The test microorganism is one whose growth is inhibited by the antibiotic effective substance produced by the unknown microorganism. If the growth of the test microorganism is inhibited by the antibiotic suspected of being produced by the unknown microorganism, the existence of the latter is positively established. If no inhibition of growth occurs, the absence of the unknown microorganism is unequivocally established.

This apparatus and procedure, however, suffer from several disadvantages. Thus, there is a "smear effect" when applying the second layer of the test microorganism to the colony to be identified. The smear effect renders it difficult to isolate the areas of inhibition of growth after application of the second layer. The smear effect also results in a further distribution of spores or conidiae of the microorganisms to be tested on the plate which grow into additional colonies. A clear and definite assignment of any inhibited areas in the test microorganism to the original colony is then rendered extremely difficult. If there are several microorganisms in the first coating layer, a smearing of the layer by the overcoat of culture medium containing the test microorganism will render it impossible to ascertain which microorganisms cause the inhibited growth areas in the test layer.

It is an object of the present invention to provide a simple efficient method for the screening and identification of microorganisms.

SUMMARY OF THE INVENTION

The present invention provides a method for screening or identifying a microorganism comprising providing two agar layers or layers of other suitable solidified known nutrient medium such as gelatine in communication with and separated by a sterilizable membrane filer; implanting in one of said agar or other solidified nutrient layers:

(a) a first unknown microorganism suspected of producing a substance effective by its reaction with a second known microorganism or enzyme detecting agent to identify said first microorganism, or (b) a first known microorganism which produces a substance effective by its reaction with a second unknown microorganism to identify said second unknown microorganism;

implanting in the other agar or other solidified bacteria nutrient layer said second microorganism or enzyme detecting agent, said membrane filter being impermeable to each of said microorganisms and enzyme detecting agent but permeable to said effective substance; and causing said effective substance to be produced and diffused through said membrane filter, and observing the effect of said effective substance on said second microorganism or enzyme detecting agent.

Agar, being the most common nutrient medium used for bacteria, is the preferred solidified nutrient layer. It is to be understood, however, that any conventional microorganism nutrient medium ca be employed to form the respective layers.

The present invention also provides an apparatus for conducting the above-described method comprising two agar or other solidified bacteria nutrient layers in communication with and separated by a sterilizable membrane filter, one of said bacteria nutrient layers being adapted for the implantation therein of (a) or (b), above, and the other bacteria nutrient layer being adapted for the implantation therein of said second microorganism or enzyme detecting agent, said membrane filter being impermeable to each of said microorganisms or enzyme detecting agents but permeable to said effective substance.

Furthermore, by the described apparatus and method known amino acid excreting bacteria (microorganisms) can be grown in one layer to detect unknown bacteria in the second layer, i.e., unknown bacteria that need the excreted amino acids for their growth. These strains are known as auxotrophic bacteria-mutants and they are of great importance in genetic research.

Instead of amino acid excreting microorganisms amino acids can be incorporated directly in the first layer. The advantage in comparison to the overlaying technique is that there is no smear effect as described above. The auxotrophic mutants on the second layer can be isolated easily without risk of contamination by a smear effect from colonies nearby.

The addition of the needed amino acids to the first layer for the growth of the auxotrophic mutants in the second layer is possible at any time without contaminating and destroying this second layer. No other conventional system enables the differentiation of autotrophs from the auxotrophs on the second layer.

DETAILED DESCRIPTION OF THE DRAWINGS

Figure 1:
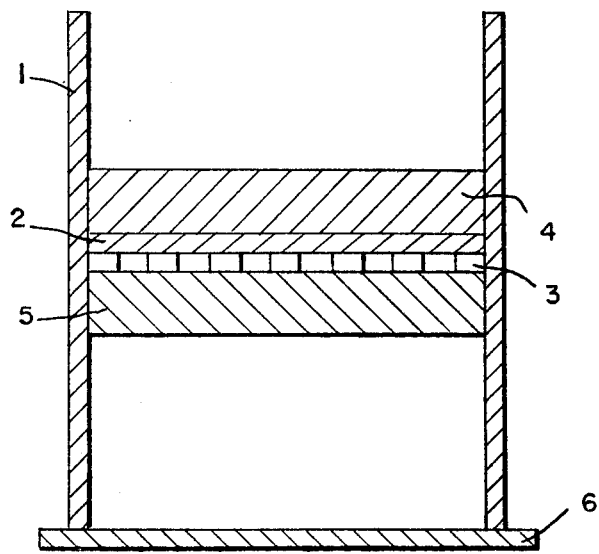
Figure 2:
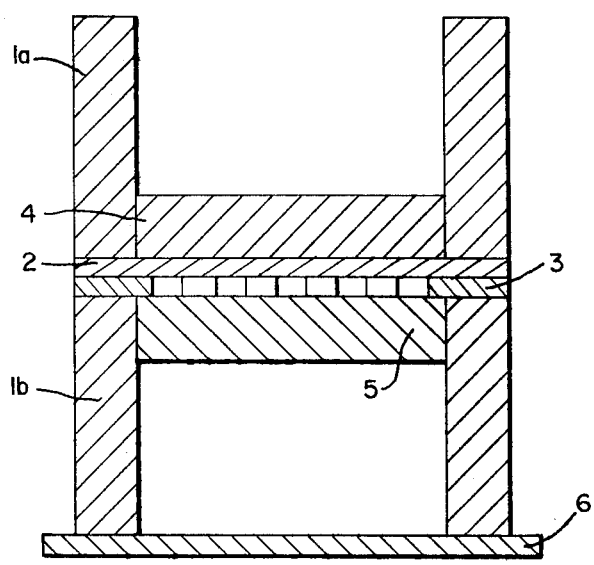

FIGS. 1 and 2 are elevational views, in section, of two embodiments of the apparatus of the invention.

DETAILED DESCRIPTION OF THE INVENTION

Referring to the drawing, the apparatus consists of a holding device, for example, the hollow body (1) which may, for example, be a pice of tube, which, at a sufficient distance from the base plate (6), has a mounting for a lattice, a netting or a perforated plate (3). According to the embodiment in FIG. II, the netting or the perforated plate (3) rests on the lower part of the hollow body (piece of tube) (1b), while the second part of the hollow body (1a) is mounted on the filter and/or the netting or perforated plate (3). The microorganism impermeable membrane filter (2) rests on the perforated plate (3) and the layer of agar (4) is applied to it. The second layer of agar (5) is applied under the perforated plate (3).

The presence of the netting or the perforated plate (3) is not critical. The membrane filter may also be mounted or clamped in the holding device without this auxiliary device.

The hollow form (1) or the hollow form pieces (1a and 1b) may be made of metal (for example, aluminum) or also of a different material (for example, polystyrene, polypropylene, high-grade steel, teflon). The diameter may range from 2 to 20 cm.

The hollow form pieces (1a) and (1b) may, for example, be metal rings (aluminum) or plastic rings.

The holding device for the netting, lattice or perforated plate (3) and for the filter (2) in the hollow form (1) is expediently mounted at a distance of 1 to 3 cm from the base plate (6); if the holding device is, for example, made out of two peices of tube, the height of the lower piece of tube (1b) is, for example, between 1 and 3 cm, preferably 2 cm. The piece of tube (1a) that rests thereon has the same height or can, if necessary, also be of a different height than the lower piece of tube (1b). There must, however, definitely be a minimum distance of 0.5 cm between the upper edge of the layer of agar and the upper end of the hollow form (1a). The wall thickness of the hollow form is, for example, between 0.2 and 1.0 cm. If the holding device consists of two hollow forms (pieces of tube) according to FIG. II, the wall thickness of both hollow forms is expediently somewhat thicker, for example, between 0.5–2.0 cm.

The lower base plate (6) is preferably a glass plate. The device according to the invention may also be covered by a glass plate on top (not shown). It is, however, also possible to place the entire device in a glass container that can be closed off on top by a glass plate (not shown), or transparent plastic plates that are made out of polystyrene, for example.

The perforated plate, net or lattice (3) advantageously comprises metal (for example, aluminum or high-grade steel) or plastic (such as, for example, polystyrene; for example, when one-way screening plates are used similar to the use of one-way Petri dishes in bacteriology). The thickness of the perforated plate, netting or lattice may be between 0.1–0.5 cm. If the device (3) is a perforated plate, the distances between the individual holes must be as small as possible (for example, 0.1–0.2 cm) and the diameter of the holes must be as large as possible (for example, between 1–1.5 cm). Generally, the perforated plate has one hole per cm² each with a diameter of 1 cm.

The shape of the holes is not critical. Preferably they are round. Any microorganism impermeable membrane filter that can be sterilized can be used as the membrane filter (2). The filter should have pore sizes from 0.22 to 0.45 to ensure microorganism impermeability. The type and design of the filter is not significant. It is only necessary that there exist between the two agar layers (4) and (5) a direct, aqueous contact. By means of this contact, it is assured that the effective substances to be determined can diffuse through the membrane filter to the other microorganisms. Generally, any filter which is suitable for aqueous media and can be sterilized without bacteriological residues is acceptable.

One of the two layers of agar (4) and (5) is adapted for receiving the effective-substance-producing colonies, for example. from a dilution series. Generally, it is preferred to use the upper layer of agar (4) for the effective-substance-producing organisms. In this case, any nutrient medium that is optimal for the production of the effective substance can be applied on the layer of agar. Also, any nutrient medium that is optimal for the growth of the microorganisms is included in the respective agar layers. The effective-substance-producing microorganism and the other microorganism can be grown or produce effective substances in their own respective optimal nutrient medium. The nutrient substances for the agar layers should have an agar concentration of form 1% to 2%, preferably 1.5%. This amount ensures that, on the one hand, there is sufficient consistency for the necessary stability of the agar layer and, on the other mand, sufficient free water for the growth of the respective microorganisms. The thickness of the two layers of agar (4) and (5) is not critical. Any thickness suitable for the cultivation of microorganisms, for example, 0.2 to 0.4 cm, preferably 0.3 to 0.4 cm, is suitable.

Any suitable nutrient containing agar or other medium material may be utilized to form the layers (4) and (5). The layers (4) and (5) may be identical, or they may also be different. As layers for the effective substance producers, the following nutrient media are particularly preferred: Special nutrient media for various types of fungi, for example, streptomycites. Bibliography: Enrichment Culture and Selection of Mutants, Symposium 1964, Gottingen, Gust. Fischer, Stuttgart, Pages 228–252. As media for the test microorganisms, the following nutrient media are, for example, considered: nutrient agar, caso-agar gelatin media, etc.

The effective-substance-producing organisms to be determined are, for example, from a media screening sample, over a dilution series, applied to the layer of agar (4). It is expedient to have 5–10 colonies of effective-substance producers on the layer of agar. The test microorganisms are generally applied into the lower layer of agar (5), expediently before the application of this layer of agar.

The effective substances produced by the microorganisms diffuse from the one layer of agar (for example, agar layer (4)), into the second layer of agar (for example, agar layer (5)), and become effective there, i.e., several inibited areas or one inhibited area form on the agar layer that contains the test microorganisms or test microorganism. In this case, it is mandatory to select the pore size of the membrane filter in such a way (for example, $0.2\mu$), that a growth of the organisms from the one into the other layer is prevented.

This prevents a coating or growing-into-eachother of the effective-substance producing strain and the test microorganism.

The device according to the invention is preferably cylindrical, however, a cubic or other shape is also possible. The size of the membrane filter or the netting, lattice or perforated plate is limited by the size of the colony of the effective-substance-producing culture. Generally, the lower limit is a diameter of 1 to 2 cm. In this range, macroscopically, an influence of an effective substance on the test microorganisms can still be recognized on the other side of the membrane in the test agar. The size of the filter or perforated plates, lattices or nettings is constructively limited by the stability of these materials and by their manageability. A reasonable diameter is, for example, about 20 cm. On such a filter, about 7-9 effective-substance-producing colonies can be tested simultaneously.

The isolation of the colony recognized as the effective-substance producer can be carried out easily and without difficulty according to the present invention.

Generally, the process according to the invention is carried out as follows: The one agar layer of the device according to the invention is injected with the various cultures of microorganisms, and the device is then, after being covered by two sterile glass plates or being placed in a sterile container that can be closed, incubated for several days (7-10 days) at temperatures between 15°-35° C., for example, in an incubator. Then the second layer of agar, which contains the test microorganism, is applied to the other side of the membrane and the apparatus incubated again, this time at temperatures between 15°-40° C. This second incubating phase generally requires only about 24 hours to two days. Subsequently, one is able to recognize at the agar layer that contains the test microorganism the formation of so-called inhibited areas thereby ascertaining whether and which colonies of the agar layer injected with microorganisms have produced effective substances.

The process according to the invention is especially suitable for the identification of organisms that produce effective antibiotic substances. The test system according to the invention may be used in the screening of producers of new antibiotics. For example, in such a system, there are used as test strains microorganisms that are resistant to known antibiotics. Thus, producers of antibiotics are recognized which produce an effective substance that do not produce reactions identical to those expected from the test microorganisms. The system according to the invention may also, for example, be used in the identification of microbiological amino-acid-producers and vitamin-producers, or in screening of high-performance mutants for fermentation. Other applications are, for example, in the genetics of fungi and bacteria, if the task is to recognize mutants that separate or enrich certain metabolic products; or to recognize, for example, the recognition of the mutagenous effect of mycotoxins that are produced by food contaminants, the present invention provides an advantageous means for a bacterial test such as the Ames-test.

In addition, the device according to the invention is a significant improvement when it comes to the recognition of pathogenic staphylococci in the food industry (meat processing) and in medicine (hospitals).

In contrast to the previously known methods, the device or the process of the invention has the following advantages:

1. The effective-substance producer and the other microorganism are microbiologically separate from each other, i.e., they may each be cultivated in a separate nutrient media:
   The effective-substance producer in a medium that is optimal for the production of effective substance or metabolites, and the other microorganism in a medium that is optimal for the test reaction.
2. Proof of the effective substances is possible directly through diffusion in the test agar, i.e., the proof of the effective-substance producer.
3. A microbiologically clean injection of the effective-substance producers (fungi or bacteria) is possible at any time.
4. When the second layer is applied, there are no "smear effects" as with the prior art devices.

EXAMPLE

Four different strains of fungi—isolated from forest soil—were examined by means of a device according to the invention for their ability to produce metabolites with antibiotic effect.

The upper side of a device according to FIG. II with a taut and sterilized membrane filter (Sarton Co.) 25 g, Type SM 11607, format 150, pore size $0.2\mu$ was layered with the Special Nutrient Screening Medium SM 1. The quantity of nutrient medium was 75 ml. As essential components, the special nutrient medium contained cornsteep liquor, soyflour, glycerin and $CaCO_3$. The proportion of agar was 1.5%. After cooling, the agar was injected with strains 71, 136, 136 and 68 of a 3-4 day old inclined-tube culture that contained a similar agar. The device was then covered on both sides by two sterile glass plates of $20\times20$ cm each and incubated in the incubator at 25° C., a temperature that is advantageous for the growth and the formation of antibiotics, for 10 days. Since most antibiotics are formed toward the end of the logarithmic growth phase or in the stationary phase, it was to be expected that, at that time, antibiotics may possibly have been present. The point in time for the proof of the formed antibiotics therefore seemed to be indicated.

As test strain for the proof of produced antibiotics, a gram-negative germ of the *Serratia Marcescens* species was used. In regard to hospitals, the gram-negative germs are of considerable significance. New antibiotics against these germs are therefore of great benefit.

75 ml nutrient-agar (Merck Type No. 5450, meat extract 3.0 g p peptine from meat 5.0 g p.l. and agar-agar 12.0 g p.l.) were, after being dissolved, brought to a temperature of 45° C., injected with 0.2 ml of a Serratia injection suspension, mixed and poured on the other side of the device. After the cooling, the "double dish" that is covered on both sides, was incubated for 24 hours at 35° C. The injection solution was maintained by a 24-hour shaking of *Serratia Marcescens* with a 5 ml nutrient bouillon.

In the test-agar layer, there was a clear inhibited area of a diameter of 3.5 cm that was exactly opposite the colony of fungus strain No. 71. This shows that this fungus strain No. 71 produced and separated a compound which, after the diffusion in the test agar, during the incubation at 35° C., inhibited the growth of the test germ at this point.

An example of an enzyme detecting agent is coagulase, an accepted diagnostic for the identification of pathogenic Staphylococcus. The presence of this enzyme is used frequently as an indication of pathogenicity.

Staphylococci producing coagulase (enzyme) can easily be detected by the described apparatus and method.

The first layer consisting of blood agar is inoculated on the surface by a specimen containing suspected staphylococci.

After incubation and the appearance of colonies—a second layer of agar containing plasma or other substrates for coagulase is added to the other side of the membrane. The excreted coagulase from coagulase positive colonies penetrates from the blood agar layer to the plasma agar layer. The plasma is coagulated at these points thereby enabling the identification of pathogenic staphylococci.

This is an example for the identification of microorganisms by a known substrate enzyme detecting agent (plasma) that reacts with the excreted enzyme (coagulase). The advantages are those described before, i.e., no smear effect and the growth and identification are done in one system. With the conventional methods this procedure is done in two separate systems:

1. growth→isolation→2. coagulase reaction

Therefore, the method of the invention saves time. This is of absolute necessity in identifying pathogenic organisms in a specimen from a highly dangerous infection.

The present apparatus and method is also suitable for identifying other pathogenic organisms with other characteristic enzymes.

I claim:

1. A method for screening or identifying a microorganism comprising providing two microorganism nutrient medium layers in communication with and separated by a sterilizable membrane filter; implanting in one of said layers:
  (a) a first unknown microorganism suspected of producing a substance effective by its reaction with a second known microorganism or enzyme detecting agent to identify said first microorganism, or
  (b) a first known microorganism which produces a substance effective by its reaction with a second unknown microorganism to identify said second unknown microorganism;

implanting in the other layer said second microorganism or enzyme detecting agent, said membrane filter being impermeable to each of said microorganisms and enzyme detecting agent but permeable to said effective substance; causing said effective substance to be produced and diffused through said membrane filter, and observing the effect of said effective substance on said second microorganism or enzyme detecting agent.

2. The method of claim 1 wherein (b) is a known microorganism.

3. The method of claim 1 wherein (b) is an enzyme detecting agent.

4. The method of claim 1 wherein said effective substance is or is suspected of being an antibiotic.

5. The method of claim 1 wherein said effective substance is or is suspected of being an amino acid.

6. The method of claim 1 wherein said effective substance is or is suspected of being a vitamin.

7. The method of claim 1 wherein said effective substance is or is suspected of being a toxin.

8. The method of claim 1 wherein said effective substance is or is suspected of being an enzyme.

* * * * *